United States Patent [19]

Towers et al.

[11] Patent Number: 5,202,348

[45] Date of Patent: Apr. 13, 1993

[54] THIARUBRINE ANTIFUNGAL AGENTS

[75] Inventors: G. H. Neil Towers, Vancouver, Canada; Reimer C. Bruening, San Carlos, Calif.; Felipe Balza, Vancouver, Canada; Zyta A. Abramowski, Vancouver, Canada; Isabel Lopez-Bazzochi, Vancouver, Canada

[73] Assignee: The University of British Columbia, Vancouver, Canada

[21] Appl. No.: 568,940

[22] Filed: Aug. 17, 1990

Related U.S. Application Data

[63] Continuation-in-part of Ser. No. 447,893, Dec. 7, 1989, abandoned.

[51] Int. Cl.$^5$ .................. A61K 31/385; C07D 339/08
[52] U.S. Cl. ...................................... 514/436; 549/20; 549/22
[58] Field of Search .................... 549/22, 20; 514/436

[56] References Cited

PUBLICATIONS

Constabel et al., 1989, Planta Medica 55: 35–37.
Rodriguez et al., 1985, Exper. 41: 419–420.
Constabel et al., 1989, Phytochem. 28: 93–95.
Balza, F. et al. *Phytochemistry*, 28 (12), pp. 3523–3524 (1989).
Rodriguez, E. *Chemical Abstracts*, 110: 149716k, p. 285 (1989) abstract of ACS *Symp. Ser.*, 1988, pp. 432–437.
Cosio, E. G., et al. *Chemical Abstracts*, 105: 168856u, p. 432 (1986) abstract of *J. Plant Physiol.*, 1986, 124(1–2), 155–64.

*Primary Examiner*—Richard L. Raymond
*Assistant Examiner*—Mark W. Russell
*Attorney, Agent, or Firm*—Pennie & Edmonds

[57] ABSTRACT

This invention pertains to a novel group of Thiarubrine substances and closely related derivatives, useful as antifungal and antibiotic agents.

14 Claims, No Drawings

THIARUBRINE ANTIFUNGAL AGENTS

CROSS REFERENCE TO RELATED APPLICATION

This application is a continuation-in-part of application Ser. No. 07/447,893, filed Dec. 7, 1989, which is incorporated herein by reference.

FIELD OF THE INVENTION

This invention pertains to a novel group of Thiarubrine substances and closely related derivatives that are useful as antifungal and antibiotic agents. The invention further pertains to a novel method for isolating the Thiarubrine substances.

BACKGROUND OF THE INVENTION

A publication entitled "Two dithiacyclohexadiene Polyacetylenes from *Chaenactis douglasii* and *Eriophyllum lanatum*", Norton, R.A.; Finlayson, A.J.; Towers, G.H.N.; Phytochemistry, 24(2), 356–7 (1985) discloses two dithiapolyacetylenes isolated from the roots of *C. douglasii* and from the plant roots as well as root cultures of *E. lanatum*. The two dithiapolyacetylenes have the respective chemical names 3 - (1- -propynyl) 6 (5-hexen-3-yn-1-ynyl)1,2-dithiacyclohexa-3,5- diene and 3 (pent-3-yn-1-ynyl) 6 (3-buten-1-ynyl)-1,2- dithiacyclohexa-3,5-diene. The trivial names Thiarubrine A and Thiarubrine B, respectively, have been given to these compounds.

Another publication entitled "Production of Antibiotic Thiarubrines by a Crown Gall Tumor Line of *Chaenactis douglasii*", Cosio, E.G.; Norton, R.A.; Towers, E.; Finlayson, A.J.; Rodriguez, E.; Towers, G.H.N.; J. Plant Physiol., 124 (1–2), 155–64 (1986) discloses dithiacyclohexadiene polyacetylenes which display considerable antimicrobial activity. A culture that accumulates these compounds was obtained by selection of red-colored areas from crown gall tumor cultures of *Chaenactis douglasii*. The tumors were induced by *Agrobacterium tumefaciens* strain A277. The main acetylenic products found were two Thiarubrines, A and B, and their corresponding thiophenes. Average yields of thiarubrines and thiophenes were 2.5 and 0.24 mg/.g dry weight, respectively, which are similar to the values seen in intact plants. The products accumulate in intercellular spaces arranged around a core of vascular tissue, forming red nodules of varying size. The structures crudely resemble the tissue organization of the roots of this plant, the only organ where these compounds accumulate. Formation of rootlets, however, did not take place at any stage during the growth of the tumors. Apparently, accumulation of these polyacetylenes by the tumor line is not a direct result of cellular transformation but a secondary effect of the existing degree of tissue differentiation.

The publication "Thiarubrine Accumulation in Hairy Root Cultures of *Chaenactis douglasii*", Constabel, C.P.; Towers, G.H.N.; J. Plant Physiol., 133(1), 67–72 (1988) discloses hairy root cultures of *C. douglasii* established using Agrobacterium rhizogenes strain TR7. One culture line accumulated twice the levels of the antifungal polyines, Thiarubrines A and B, compared to non-transformed control root cultures, while maintaining rapid growth. The combination of fast growth and high thiarubrine accumulation could not be duplicated in controls by adding exogenous NAA to the culture medium. Hairy root cultures also produced less Thiarubrine B relative to Thiarubrine A compared to controls.

A publication entitled "Antiviral Properties of Thiarubrine A, a Naturally Occurring Polyine", Hudson J.B.; Graham E.A.; Fong R; Finlayson A.J., Towers G.H.N.; Planta Med 0(1), 1986, 51–54 relates to the naturally occurring polyine, Thiarubrine A. It was evaluated for its antiviral properties in the presence and absence of long wave UV radiation (UV-A). Four viruses and a mammalian cell line were used as targets. The two mammalian viruses, murine cytomegalovirus and Sindbis virus, both of which possess membranes, were extremely sensitive to the compound, but only in the presence of UV-A radiation. The bacteriophage T4 was slightly affected in UV-A only, whereas the bacteriophage M13 was completely unaffected. Thus Thiarubrine A is photoactive against membrane containing viruses. In contrast mouse cells were moderately sensitive to the compound in the presence of UV-A, and somewhat less sensitive in the dark.

Thiarubrine A is also discussed in "Antibiotic Properties of Thiarubrine A a Naturally Occurring Dithiacyclohexadiene Polyine", Towers G.H.N.; Abramowski Z; Finlayson A.J.; Zucconi A; Planta Med 0 (3), 1985, 225–229. Thiarubrine A, a dithiacyclohexadiene polyine from the roots of *Chaenactis douglassii*, is disclosed as exhibiting strong antifungal activity towards *Candida albicans* and *Aspergillus fumigatus* at concentrations comparable to those of amphotericin B. It also exhibits cytotoxic activity towards *Escherichia coli*, *Bacillus subtilis* and *Hycobacteria sp.* and the nematode *Coenorhabditis elogans*. A thiophene derived from thiarubrine A was phototoxic, requiring UV-A light for biological activity. The effects of Thiarubrine A, thiophene A and alpha-terthienyl on the above organisms, as well as on CHO cells, were compared.

Polyacetylene groups and thiophenes are disclosed in "comparison of the antiviral effects of naturally occurring thiophenes and polyacetylenes", Hudson J. B.; Graham E.A.; Chan G; Finlayson A.J.; Towers G.H.N.; Planta Med 0 (6], 1986 (Recd. 1987), 453–457. Five naturally 35 occurring compounds, containing various thiophene and polyacetylene groups, were compared with respect to their phototoxic activities against two animal viruses, murine cytomegalovirus and Sindbis virus, both of which possess membranes. Alpha-Terthienyl was extremely toxic to both viruses, but only in the presence of long wave ultraviolet radiation. The order of potency was alpha-terthienyl thiarubrine-A > phenylheptatriyne > ACBP-thiophene > thiophene-A (hydrolysis product of thiarubrine A). The murine-CMV, which had been inactivated by any of these compounds, was still capable of penetrating cultured mouse cells efficiently and reaching the cell nucleus, the normal site of virus replication. The results are discussed in terms of possible mechanisms of action of phototoxic thiophenes and polyacetylenes.

Canadian Patent No. 1,169,767, issued Jun. 26, 1984, Towers et al., discloses cercaricidal compositions containing naturally occurring conjugated polyacetylenes and method for controlling cercariae using the same.

Canadian Patent No. 1,172,460, granted Aug. 14, 1984, Towers et al., discloses a method for controlling weeds using naturally occurring conjugated polyacetylenes.

Canadian Patent No. 1,173,743, granted Sep. 4, 1984, Towers et al., discloses a method for controlling pests using naturally occurring conjugated polyacetylenes.

SUMMARY OF THE INVENTION

The invention is directed to a novel substance having antifungal and anti-bacteria activity of the formula:

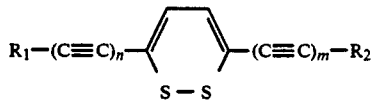

wherein $R_1$ is $CH_3$ or $CH_2R_3$;
$R_2$ is

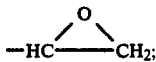

—$CHR_3$—$CH_2R_3$; —$HCHa$—$CH_2R_3$; —$CHR_3$—$CH_2Ha$; $CH=CH_2$;
$R_3$ is H; OH; —CHO; COOH or $COOR_4$ wherein $R_4$ is derived from an alcohol;
Ha is F; Cl; Br; or I;
n is 1 or 2; and
m is 1 or 2, and pharmaceutically acceptable salts thereof, provided that when $R_1$ is $CH_3$, n is 1 and m is 2, then $R_2$ is not $CH=CH_2$; and provided that when $R_1$ is $CH_3$, n is 2 and m is 1, then $R_2$ is not $CH=CH_2$.

The invention is also directed to the bactericide or fungicide Thiarubrine D

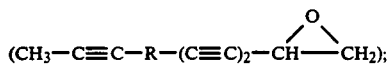

the fungicide Thiarubrine E

the fungicide Thiarubrine F

the fungicide Thiarubrine G

and the fungicide Thiarubrine H

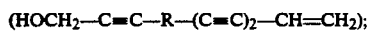

where R is

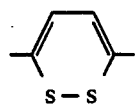

Bacteria may be treated with the Thiarubrine substance in association with light of a wavelength range about 320 to 400 nanometers, or specifically, in association with light of a wavelength about 350 nanometers.

The invention is also directed to an antifungal composition comprising a Thiarubrine substance of the formula:

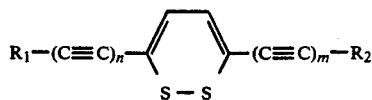

wherein $R_1$ is $CH_3$ or $CH_2R_3$;
$R_2$ is

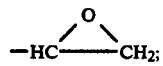

—$CHR_3$—$CH_2R_3$; —$HCHa$—$CH_2R_3$; —$CHR_3$—$CH_2Ha$; $CH=CH_2$;
$R_3$ is H; OH; —CHO; COOH or $COOR_4$ wherein $R_4$ is derived from an alcohol;
Ha is F; Cl; Br; or I;
n is 1 or 2; and
m is 1 or 2 and pharmaceutically acceptable derivatives thereof, provided that when $R_1$ is $CH_3$, n is 1 and m is 2, then $R_2$ is not $CH=CH_2$; and provided that when $R_1$ is $CH_3$, n is 2 and m is 1, then $R_2$ is not $CH=CH_2$ in association with a pharmaceutically acceptable carrier.

In the composition, Ha may be chlorine, $R_3$ may be OH, $R_3$ may be OH, n may be 1 and m may be 2. The carrier may be distilled water, saline or any other pharmaceutically acceptable carrier.

The composition can be used to control *E. coli, Staphylococcus aureus, Streptococcus faecalis, Mycobacterium sp.* or *Enterobacter aerogenes* in dark and more effectively in the presence of light having a wavelength of about 320 to 400 nanometers, or specifically, having a wavelength of about 350 nanometers. The composition can be used to control *Candida albicans, Aspergillus fumigatus* or *Cryptococcus neoformans* as well.

The foregoing Thiarubrine substance is present in the composition at a concentration of about 1 to 100 nanograms/ml of carrier, or specifically, at a concentration of about 10 nanograms/ml of carrier.

The invention is also directed to a method of controlling *Candida albicans* or Aspergillus which comprises exposing a host infected with the *Candida albicans* or Aspergillus to an antifungal effective amount of a compound of the formula:

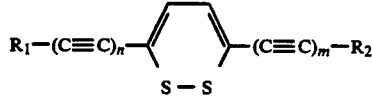

wherein $R_1$ is $CH_3$ or —$CH_{20}H$; and $R_2$ is

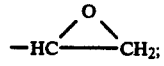

$CHOH$—$CH_2OH$; —$HCCl$—$CH_2OH$; $CHOH$—$CH_2Cl$ or $CH=CH_2$.

*Candida albicans* may be treated at a concentration of Thiarubrine to *Candida albicans* in the range of about 1.0 to about 100 nanograms/ml of distilled water.

The invention pertains to an antifungal composition comprising Thiarubrine D and a pharmaceutically acceptable carrier. The Thiarubrine D can be present in the composition at a concentration of 7 nanograms/ml of carrier. The carrier in the composition can be water or any other pharmaceutically acceptable carrier.

DETAILED DESCRIPTION OF SPECIFIC EMBODIMENTS OF THE INVENTION

Novel Thiarubines

The present invention is based on the discovery of a group of novel dithiacyclohexadiene compounds isolated from extracts of a common ragweed *Ambrosia chamissonis* Asteraceae (tribe Heliantheae) found in coastal areas ranging from southern California to British Columbia, Canada. The novel compounds, isolated from extracts of root tissues, have been found to possess remarkable antifungal and antibactericidal activity.

The compounds which are somewhat similar in structure to dithiacyclohexadienes, i.e., Thiarubrine A and B, previously isolated from members of the Asteraceae family including *Chaenactis douglasii, A. chamissonis* and other species have been generically designated by the coined name Thiarubrine.

The novel Thiarubrine substances, and their closely related homologues which have been discovered, can be represented by the following generic formula:

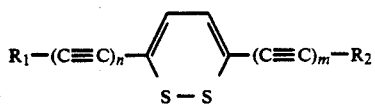

wherein $R_1$ is $CH_3$ or $CH_2R_3$;
$R_2$ is:

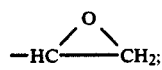

—$CHR_3$—$CH_2R_3$; —$HCH_a$—$CH_2R_3$; —$CHR_31'CH_2H_a$; —$CH=CH_2$;
$R_3$ is H; OH; —CHO; COOH or $COOR_4$ wherein $R_4$ is derived from an alcohol;
$H_a$ is F; Cl; Br; I;
n is 1 or 2; and
m is 1 or 2, provided that when $R_1$ is $CH_3$, n is 1 and m is 2, then $R_2$ is not $CH=CH_2$; and provided that when $R_1$ is $CH_3$, n is 2 and m is 1, then $R_2$ is not $CH=CH_2$.

A series of five novel substances have been chemically identified, assigned the generic trivial name Thiarubrine and have been given letter designations as follows:

1. Thiarubrine D: ($CH_3$—C≡C—R—(C≡C)$_2$

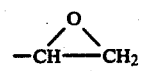

);
2. Thiarubrine E: ($CH_3$—C≡C—R—(C≡C)$_2$—CHOH—$CH_2OH$);
3. Thiarubrine F: ($CH_3$—C≡C—R—(C≡C)$_2$—CHCl—$CH_2OH$);
4. Thiarubrine G: ($CH_3$—C≡C—R—(C≡C)$_2$—CHOH—$CH_2Cl$); and
5. Thiarubrine H: ($HOCH_2$—C≡C—R—(C≡C)$_2$—CH=$CH_2$);
wherein R is

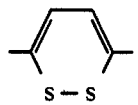

Method for Preparing the Novel Thiarubrines

The therapeutically effective thiarubrine antifungal and antibacterial agents are prepared by a method comprising steps as follows:

(a) tissues of plant(s) of the Asteraceae family that contain thiarubrines, e.g., *Ambrosia chamissonis* (var.), including the whole plant, plant parts, or tissue cultures thereof, are rinsed with water and are either airdried, frozen, or stored in various organic solvents (i.e. hexane, methanol, etc.);

(b) the roots and or various plant parts (i.e. roots, leaves, stems, etc.) obtained as in (a) are either lyophilized directly or the root bark is peeled and/or lyophilized, or blended or used directly;

(c) the plant parts as in (a) or (b) are extracted by either percolation with various organic solvents (i.e. hexane, ethyl acetate, methanol, etc.), or by cold organic solvent extraction using various solvents (hexane, methanol, etc.) followed by filtration or centrifugation, or by supercritical fluid extraction (SFE) (i.e. carbon dioxide or ammonia as extractants);

(d) the organic solvent-containing extracts obtained from step (c) are concentrated in vacuo, and subjected to gel filtration (e.g. on Sephadex) with water +water +miscible organic solvents as the mobile phase; or alternatively (e) the organic solvent-containing extracts obtained from step (c) are concentrated in vacuo, subjected to reversed-phase TLC, column or HPLC chromatography, using water, and/or water + water-miscible organic solvents, all with or without buffers, as the mobile phase; or alternatively, (f) the organic solvent-containing extracts obtained from step (c) are concentrated in vacuo, subjected to silica gel TLC, column or HPLC chromatography with various organic solvents (i.e. freon, low-boiling hydrocarbons, alone or in mixture with polar modifiers, e.g. diethyl ether, ethyl acetate, etc.) as the mobile phase; or alternatively (g) the organic solvent-containing extracts obtained from step (c) are concentrated in vacuo, subjected to SFE (supercritical fluid extraction) or SFC (supercritical fluid chromatography) with various gases alone or in mixture with polar modifiers (i.e. water, methanol, etc.); or alternatively (h) the organic solvent-containing extracts obtained from step (c) are concentrated in vacuo, subjected to counter-current partition chromatography using anhydrous biphasic systems (i.e. hexane/acetonitrile, etc); or alternatively (i) the organic solvent-containing extracts obtained from step (c) are concentrated in vacuo, and subjected to gas chromatography;

(j) the thiarubrine-containing fractions display a red or red/brown chromophoric band and are detected by uv or visible $\lambda$=200-550 nm) detectors;

(k) the thiarubrines are obtained by collecting, and concentrating the uv/vis active fractions as in step (d); or alternatively (l) the thiarubrines are obtained by collecting, and concentrating the uv/vis active fractions as in step (e); or alternatively (m) the thiarubrines are obtained by collecting, and concentrating the uv/vis active fractions as in step (f); or alternatively (n) the thiarubrines are obtained by collecting, and concentrating the uv-vis active fractions as in step (g); or alternatively (o) the thiarubrines are obtained by collecting, and concentrating the uv/vis active fractions as in step (h); or alternatively (p) the thiarubrines are obtained by collecting, and concentrating the uv/vis active fractions as in step (i).

Applications of Thiarubrines

The novel Thiarubrine compounds of the invention display strong antifungal activity in the dark and strong antifungal and bactericidal activity in association with ultra-violet A light in the wave length range 320 to 400 nm, and notably 350 nm.

These substances are effective in killing strains of Candida albicans. *Aspergillus fumigatus* and *Cryptococcus neoformans* in the dark. They are effective in killing *Escherichia coli, Staphylococcus aureus, Streptococcus faecalis, Mycobacterium sp,* and *Enterobacter aerogenes.*

Thus, the Thiarubrine compounds are advantageously used for treatment of infections induced by the above mentioned fungal and bacterial agents. For example, the epoxide compound, designated Thiarubrine D, is a novel complex sulphur-containing substance. Thiarubrine D can be described by the specific formula:

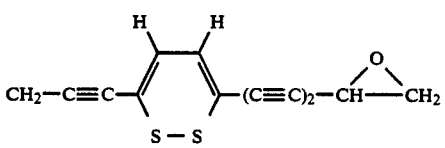

Its very high antifungal activity in extremely low concentrations indicates a usefulness in vivo, i.e. for human patients.

The chemical, Thiarubrine D, is light sensitive and breaks down under light to the corresponding thiophene. It is therefore necessary to store the chemical in the dark and for effectiveness to conduct antifungal therapy in the absence of blue and ultraviolet light.

We have demonstrated in a series of tests which are tabulated below that Thiarubrines D, E, F, G and H will inhibit the growth of *Candida albicans,* at very low levels, i.e. in the nanogram/ml range.

The following Examples are presented to illustrate the present invention and in no way intended to be a limitation thereon.

EXAMPLES

Preparation of Novel Thiarubrines

*A. chamissonis* were collected from Marin County, Calif. and from Tiaswwassen, British Columbia.

Freeze-dried roots (350-500 g) were extracted with cold MeOH, concentrated in vaccuo at 30° C. and redissolved in MeCN. The combined extracts were taken up in $CHCl_3$, dried and evaporated. The residue was chromatographed on a silica gel 60 column (Merck 70 -230 mesh), eluted with n-heptane-n-hexane (1:4) gradually changed to n-hexane-EtOAc (2:3) and finally EtOAc. Extracts and fractions for HPLC analysis were taken to dryness and resuspended in MeCN. Samples (20 and 100 μl) were injected on a Varian 5000 liquid chromatograph with a MCH-10 reverse phase column (4×300 mm) using $MeCN-H_2O$ (18:7) at a flow rate of 1.0 ml $min^{-1}$. A much better resolution of Thiarubrines F and G and H was achieved with $MeCN-H_2O$ (2:3 and 1:1) and each compound isolated by extraction of the recovered HPLC fractions with $CHCl_3$. All procedures were performed in dim light to prevent photodegradation of the compounds.

MeCN

Thiarubrine D: UV $\lambda_{max}$ nm: 484, 344, 272; MS m/z (rel. int.): 244 (M) +(100), 214, (75), 182 (21), 170 (98).

MeCN

Thiarubrine E: UV $\lambda_{max}$ nm: 482, 342,326(sh): MS m/z (rel. int.): 262 (M) + (100), 231, ($M-CH_2OH$) + (80), 199 ($M-CH_2OH-S$) +(15).

MeCN

Thiarubrine F: UV-vis $\lambda_{mes}$ nm: 484, 344, 230; MS m/z (rel. int.) 279.9783 (M) + (80), 249 [$M-CH_2OH$]+ (30), 248 (M-S)+ (50), 217 [$M-S-CH_2OH$]+, (48).

MeCN

Thiarubrine G: UV-vis-$\lambda_{mes}$ nm: 484, 342, 228, MS m/z (rel. int.): 279.9780 (M)+, (100), 248 (M-S)+, (18) 244 (M-HCl)+ (50), 231, [$M-CH_2Cl$]+ (98), 199 ($M-CH_2Cl-S$)+ (30).

MeCN

Thiarubrine H: UV-vis $\lambda_{mes}$ nm: 490, 354, 232, MS m/z (rel. int.): 244.0009 (M)+, (100), 227 (M-OH)+ (5), 212 (M-S)+ (65), 195 (M-S-OH)+ (6).

Biological Activity of Thiarubrines

The following experiments demonstrate the biological activity of the Thiarubrines of the present invention.

TABLE 1

Comparison of Concentrations of Thiarubrines and Fungizone Causing 50% Growth Inhibition (μg/ml) During 24 Hours Exposure

| | Thiarubrines | | | |
|---|---|---|---|---|
| | A | D | E | Fungizone |
| C. albicans | 0.028 | 0.0006 | 0.0014 | 0.037 |
| p815 | 0.035 | 0.12 | 0.024 | >5.0 |
| L1210 | 0.035 | 0.047 | 0.027 | 2.8 |
| WEHI-3 | 0.027 | 0.05 | 0.04 | 1.9 |
| 3T3 | 0.45 | 0.48 | 0.12 | >5.0 |

P815 = Mouse mastocytoma
L1210 = Mouse lymphocytic leukemia
WEHI-3 = Mouse myelomonocyte
3T3 = Mouse fibroblasts

TABLE 2

Toxicity Index of Thiarubrines and Fungizone for Different Animal Cell Lines

| | Thiarubrines | | | |
|---|---|---|---|---|
| | A | D | E | Fungizone |
| $LC_{50}$ P815 | 1 | 200 | 17 | >135 |
| $LC_{50}$ C. albicans | | | | |
| $LC_{50}$ L1210 | 1 | 78 | 19 | 76 |
| C. albicans | | | | |
| $LC_{50}$ WEHI-3 | 1 | 83 | 28 | 51 |
| $LC_{50}$ C. albicans | | | | |
| $LC_{50}$ 3T3 | 12 | 800 | 86 | >135 |

TABLE 2-continued

Toxicity Index of Thiarubrines and Fungizone for Different Animal Cell Lines

| | Thiarubrines | | | Fungizone |
|---|---|---|---|---|
| | A | D | E | |
| $LC_{50}$ C. albicans | | | | |

Table 2 shows how many times the concentrations needed to inhibit growth in 50% of animal cells are higher than doses required to inhibit growth in 50% of C. albicans.

TABLE 3

Comparison of Minimal Concentration Causing 100% Growth Inhibition (μg/ml) During 24 Hours Exposure

| | Thiarubrines | | | Thiophenes | | | |
|---|---|---|---|---|---|---|---|
| | A | D | E | D | E | Fungizone | Gentamycin |
| E. coli | 0.625 | 0.078 | 0.019 | 5.0 | >5.0 | | 1.25 |
| P. aeruginosa | 2.5 | 0.625 | 0.625 | >5.0 | >5.0 | | 2.5 |
| C. albicans | 0.16 | 0.0024 | 0.0048 | >5.0 | >5.0 | 0.16 | |
| P815 mastocytoma | 0.625 | 1.25 | 0.3125 | >5.0 | >5.0 | | |

This table shows that minimal concentration causing 100% growth inhibition of animal tumourcells - P815 line is about 500 times greater than the concentration needed for 100% growth inhibition of C. albicans in the case of Thiarubrine D, 65 times greater for Thiarubrine E, and about 4 times for Thiarubrine A.

TABLE 4

Comparison of Minimal Concentration Causing 50% Growth Inhibition (μg/ml) During 24 Hours Exposure

| | Thiarubrines | | | Thiophenes | | | |
|---|---|---|---|---|---|---|---|
| | A | D | E | D | E | Fungizone | Gentamycin |
| E. coli | 0.18 | 0.02 | 0.015 | 1.7 | >5.0 | | 0.37 |
| P. aeruginosa | 0.68 | 0.21 | 0.28 | >5.0 | >5.0 | | 1.0 |
| C. albicans | 0.028 | 0.0006 | 0.0014 | 1.1 | 4.5 | 0.037 | |
| P815 mastocytoma | 0.035 | 0.12 | 0.024 | 3.5 | 4.0 | | |

According to these data, concentration needed to inhibit growth of animal cells - P815 in 50% is 200 times higher than for C. albicans in the case of Thiarubrine D, 17 times higher for Thiarubrine E and the same for Thiarubrine A.

Doses inhibiting growth in 50% were estimated by plotting concentration on a logarithmic scale and percent of growth inhibition for 24 hours exposure on a probability scale.

TABLE 5

| Organism | ATCC No. | Thiarubrine D Minimal Inhibitory Concentration (ng/ml) |
|---|---|---|
| 1. Staphylococcus aureus | 25923 | 10,000 |
| 2. Streptococcus faecalis | 29212 | 10,000 |
| 3. Escherichia coli | 25992 | 1,000 |
| 4. Pseudomonas aeruginosa | 27853 | 10,000 |
| 5. Staphylococcus aureus | 29213 | 10,000 |
| 6. Enterobacter aerogenes | 35029 | 10,000 |
| 7. Klebsiella pneumoniae | 33495 | 10,000 |
| 8. Staphylococcus epidermis | 29972 | 10,000 |
| 9. Cryptococcus neoformans | F548 | 64 |
| 10. Candida pseudotropicalis | | 10,000 |
| 11. Staphylococcus aureus (metacylliu res.) | | 10,000 |
| 12. Pseudomonas aeruginosa | 141 | >10,000 |
| 13. Pseudomonas aeruginosa | 205 | >10,000 |
| 14. Pseudomonas aeruginosa | 3E5 | 10,000 |
| 15. Zanthomonas maltophilia | 3E6 | 10,000 |
| 16. Staphylococcus aueras (metacylliu res.) | B4287 | 10,000 |
| 17. Acinetobacter | C42 | 1,000 |
| 18. Acinetobacter | 6C10 | 1,000 |
| 19. Enterobacter cloacoe | 1A5 | 1,000 |
| 20. Enterobacter cloacoe | 9E5 | 1,000 |
| 21. Aspergillus | 05 | 32 |
| 22. Candida | 01 | 16 |
| 23. Candida | 02 | 16 |
| 24. Candida | 03 | 64 |
| 25. Candida | R4197 | 16 |
| 26. Enterobacter sp. | 9E7 | 10,000 |
| 27. Serratia marscenes | 3A3 | 10,000 |
| 28. Listeria monocytogenes | 106 | 10,000 |
| 29. Listeria monocytogenes | 301 | 10,000 |
| 30. Enterococcus faecalis | 1A3 | 10,000 |
| 31. Klebsiella sp. | | 1,000 |
| 32. Candida | F617 | 8 |
| 33. Enterococcus (gentamycin res.) | | 10 |
| 34. Aspergillus | F604 | 64 |
| 35. Enterococcus faecalis | 207 | 1,000 |

Results were obtained by agar dilution method. Mueller Hinton agar plates (pH - 7.4) with different doses of ThD were inoculated with $10^4$ cfu/spot and incubated 21 hours at 34°. MIC is the lowest concentration with no growth.

TABLE 6

Sensitivity of Aspergillus fumigatus to Thiarubrines A. D. E.

| Compound | Dose (ng/disc) | Zone of Growth Inhibition (mm) |
|---|---|---|
| Thiarubrine A | 10,000 | 27 |
| | 1,000 | 27 |
| | 100 | 19 |
| | 10 | 8 |
| | 1 | —* |
| Thiarubrine D | 10,000 | 32 |
| | 1,000 | 26 |
| | 100 | 23 |
| | 10 | 14 |
| | 1 | — |
| Thiarubrine E | 10,000 | 50 |
| | 1,000 | 50 |
| | 100 | 36 |
| | 10 | 17 |
| | 1 | — |

Results were obtained by agar diffusion method. Disc diameter - 6 mm. -* = no zone over disc diameter.

TABLE 7

LC$_{50}$ (24 hrs.) Data Obtained by Different Method Doses Required to Inhibit Growth of *C. albicans* in 50% During 24 hrs. (ng/ml)

| Organism | Thiarubrines A | D | E | Fungizone | Econazole |
|---|---|---|---|---|---|
| *C. albicans* | 40 | 7 | 6 | 64 | 56 |
| P815 mastocytoma | 81 | 85 | 28 | 50,000 | |

Data on degradation of Thiarubrine D (ThD) expressed as changes of concentration required to inhibit growth of *C. albicans* in 50% during 24 hrs. exposure (Lc$_{50}$ 24 hrs.).

TABLE 8A

Degradation of ThD under Exposure to "Bench" Cool White Light

| Time of Exposure | LC$_{50}$ (24 hrs.) ng/ml |
|---|---|
| 24 hrs. | " 5,000 |
| 6 hrs. | " 5,000 |
| 0.5 hrs. | 140 |
| 15 mins. | 26 |
| 5 mins. | 12 |
| 0 mins. | 7 |

TABLE 8B

Temperature and Time Dependent Degradation of ThD in Water Solution (Saboraud Dextrose Medium)

| Time of Exposure | LC$_{50}$ 24 Hrs. ng/ml Temperature | |
|---|---|---|
| | 37° C. | Room |
| 24 hrs. | 210 | 110 |
| 6 hrs. | 85 | 42 |
| 2 hrs. | 33 | 22 |
| 0.5 hrs. | 20 | 16 |
| 0 hrs. | 7 | 7 |

TABLE 9

Influence of Exposure of ThD for Two Hrs. to Different pH (5, 6, 7, 8) of Sodium Phosphate Buffer

| pH | LC$_{50}$ (ng/ml) |
|---|---|
| 5 | 40 |
| 6 | 34 |
| 7 | 20 |
| 8 | 52 |

TABLE 10

Changes in LC$_{50}$ Addition of Fetal Bovine Serum (FBS) to Saboraud Dextrose Medium (SAB)

| Medium | LC$_{50}$ (ng/ml) |
|---|---|
| SAB | 7 |
| SAB + 5% FBS | 14 |
| SAB + 10% FBS | 16 |

TABLE 11

Decomposition of ThD in 95% Ethanol in −20° C.

| Days | LC$_{50}$ (ng/ml) |
|---|---|
| 0 | 7 |
| 21 | 17 |

TABLE 12

Comparison of Doses of ThD Required to Inhibit Different Numbers of *C. albicans* Cells

| Cell Density | LC$_{50}$ (ng/ml) |
|---|---|
| $10^4$/ml | 7 |
| $10^5$/ml | 16 |
| $10^6$/ml | 42 |

TABLE 13

Three Thiarubrines F,G and H Were Isolated and their Effectiveness was Found

| Organism | Lc$_{50}$ 24 hrs. ng/ml Thiarubrine | | |
|---|---|---|---|
| | F | G | H |
| *C. albicans* | 6 | 8 | 4 |
| P815 mastocytoma | 140 | 90 | 59 |

TABLE 14

Biological Activities of Thiarubrines

| | A | B | C | D | E | F | G | H |
|---|---|---|---|---|---|---|---|---|
| Conc. in plant | H | L | — | H | H | L | L | L |
| Decomp. product | T | T | T | T | T | T | T | T |
| Stability | L | L | L | H | H | H | H | H |
| Anti-Candida | Y | Y | Y | Y | Y | Y | Y | Y |
| Anti-Aspergillus | Y | Y | Y | Y | Y | Y | Y | ? |
| Anti-bacterial | Y | Y | Y | Y | Y | Y | Y | ? |

Legend
H = high; L = low; T = thiophene; Y = yes; y = less active; ? = not tested As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. An isolated substance having antifungal activity of the formula

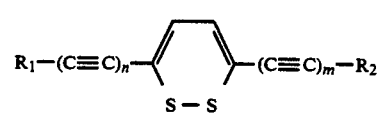

where
$R_1$ is $CH_3$ or $HOCH_2$;
$R_2$ is

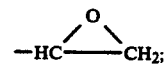

—CHOHCH$_2$OH;   —CHClCH$_2$OH;
—CHOHCH$_2$Cl; or —CH=CH$_2$
n is 1;
m is 2;
, provided that when $R_1$ is $CH_3$, then $R_2$ is not CH=CH$_2$, and pharmaceutically acceptable salts thereof.

2. An isolated Thiarubrine D substance of the formula:

3. An isolated Thiarubrine E substance of the formula:

$$CH_3-C{\equiv}C-\underset{S-S}{\bigcirc}-(C{\equiv}C)_2-\overset{OH}{\underset{OH}{<}}.$$

4. An isolated Thiarubrine F substance of the formula:

$$CH_3-C{\equiv}C-\underset{S-S}{\bigcirc}-(C{\equiv}C)_2-\overset{Cl}{\underset{OH}{<}}.$$

5. An isolated Thiarubrine G substance of the formula:

$$CH_3-C{\equiv}C-\underset{S-S}{\bigcirc}-(C{\equiv}C)_2-\overset{OH}{\underset{Cl}{<}}.$$

6. An isolated Thiarubrine H substance of the formula:

$$HOCH_2-C{\equiv}C-\underset{S-S}{\bigcirc}-(C{\equiv}C)_2-CH{=}CH_2.$$

7. An antifungal composition, comprising a Thiarubrine substance of the formula:

$$R_1-(C{\equiv}C)_n-\underset{S-S}{\bigcirc}-(C{\equiv}C)_m-R_2$$

where
$R_1$ is $CH_3$ or $HOCH_2$;
$R_2$ is $$-HC\overset{O}{\underset{}{\triangle}}CH_2;$$

—CHOHCH$_2$OH;  —CHClCH$_2$OH;
—CHOHCH$_2$Cl; or —CH=CH$_2$ n is 1;
m is 2;

, provided that when $R_1$ is $CH_3$, then $R_2$ is not CH=CH$_2$, and pharmaceutically acceptable carrier.

8. The composition of claim 7, in which the Thiarubrine substance is Thiarubrine D of the formula:

$$CH_3-C{\equiv}C-\underset{S-S}{\bigcirc}-(C{\equiv}C)_2-\overset{O}{\underset{}{\triangle}}.$$

9. The composition of claim 7, in which the Thiarubrine substance is Thiarubrine E of the formula:

$$CH_3-C{\equiv}C-\underset{S-S}{\bigcirc}-(C{\equiv}C)_2-\overset{OH}{\underset{OH}{<}}.$$

10. The composition of claim 7, in which the Thiarubrine substance is Thiarubrine F of the formula:

$$CH_3-C{\equiv}C-\underset{S-S}{\bigcirc}-(C{\equiv}C)_2-\overset{Cl}{\underset{OH}{<}}.$$

11. The composition of claim 7, in which the Thiarubrine substance is Thiarubrine G of the formula:

$$CH_3-C{\equiv}C-\underset{S-S}{\bigcirc}-(C{\equiv}C)_2-\overset{OH}{\underset{Cl}{<}}.$$

12. The composition of claim 7, in which the Thiarubrine substance is Thiarubrine H of the formula:

$$HOCH_2-C{\equiv}C-\underset{S-S}{\bigcirc}-(C{\equiv}C)_2-CH{=}CH_2.$$

13. The composition of claim 7, wherein the Thiarubrine substance is present at a concentration of about 1 to 100 nanograms/ml of carrier.

14. The composition of claim 7, wherein the Thiarubrine substance is present at a concentration of about 10 nanograms/ml of carrier.

* * * * *